(12) United States Patent
Gillberg et al.

(10) Patent No.: US 8,099,164 B2
(45) Date of Patent: Jan. 17, 2012

(54) SELECTIVELY IMPLEMENTABLE DIGITAL SIGNAL PROCESSING CIRCUIT FOR AN IMPLANTABLE MEDICAL DEVICE

(75) Inventors: Jeffrey M. Gillberg, Coon Rapids, MN (US); Steven D. Goedeke, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 43 days.

(21) Appl. No.: 11/380,864

(22) Filed: Apr. 28, 2006

(65) Prior Publication Data

US 2007/0255331 A1 Nov. 1, 2007

(51) Int. Cl.
*A61N 1/36* (2006.01)

(52) U.S. Cl. ............. 607/9; 607/4; 607/5; 607/6; 607/7; 607/8; 607/10; 607/11; 607/12

(58) Field of Classification Search .................... 607/60, 607/4–17; 600/517
See application file for complete search history.

(56) References Cited

U.S. PATENT DOCUMENTS

| | | | |
|---|---|---|---|
| 4,404,972 A | 9/1983 | Gordon et al. | |
| 4,407,288 A * | 10/1983 | Langer et al. | 607/4 |
| 5,312,441 A | 5/1994 | Mader et al. | |
| 5,441,524 A | 8/1995 | Rueter et al. | |
| 5,464,432 A | 11/1995 | Infinger et al. | |
| 5,464,435 A * | 11/1995 | Neumann | 607/9 |
| 5,924,979 A | 7/1999 | Swedlow et al. | |
| 6,016,448 A | 1/2000 | Busacker et al. | |
| 6,023,641 A | 2/2000 | Thompson | |
| 6,029,087 A | 2/2000 | Wohlgemuth | |
| 6,091,986 A | 7/2000 | Keimel | |
| 6,115,630 A * | 9/2000 | Stadler et al. | 600/521 |
| 6,167,303 A | 12/2000 | Thompson | |
| 6,223,080 B1 | 4/2001 | Thompson | |
| 6,282,661 B1 | 8/2001 | Nicol | |
| 6,363,280 B1 | 3/2002 | Mouchawar et al. | |
| 6,519,706 B1 | 2/2003 | Ogoro | |
| 6,647,292 B1 | 11/2003 | Bardy et al. | |
| 6,681,135 B1 | 1/2004 | Davis et al. | |
| 6,718,475 B2 * | 4/2004 | Cai | 713/323 |
| 6,721,597 B1 | 4/2004 | Bardy et al. | |
| 6,766,193 B1 | 7/2004 | Mouchawar et al. | |
| 6,856,835 B2 | 2/2005 | Bardy et al. | |
| 2003/0055345 A1 | 3/2003 | Eigler et al. | |

* cited by examiner

*Primary Examiner* — Niketa Patel
*Assistant Examiner* — Rex R Holmes
(74) *Attorney, Agent, or Firm* — Stephen W. Bauer; Michael J. Ostrom

(57) ABSTRACT

Embodiments of the invention include an implantable medical device having a digital signal processing circuit associated with an implantable medical device function. The digital signal processing circuit can be selectively implementable according to the clinical need of a patient. Embodiments of the invention also include methods of making and using such implantable medical devices.

8 Claims, 4 Drawing Sheets

SELECTIVELY IMPLEMENTABLE DIGITAL SIGNAL PROCESSING CIRCUIT FOR AN IMPLANTABLE MEDICAL DEVICE

FIELD OF THE INVENTION

The disclosure relates to implantable medical devices (IMDs).

BACKGROUND OF THE INVENTION

Implantable medical devices are used to collect physiological information and deliver therapy. As implantable medical devices have become more complex, each device is typically provided with a myriad of functions and capabilities. Unfortunately, the circuits providing the functions also draw current, shortening the life span of the implantable medical device's energy source. Further, while these additional capabilities are useful and required by many patients, other patients do not need the full range of capabilities provided.

DETAILED DESCRIPTION OF THE ILLUSTRATED EMBODIMENTS

Figure 1:
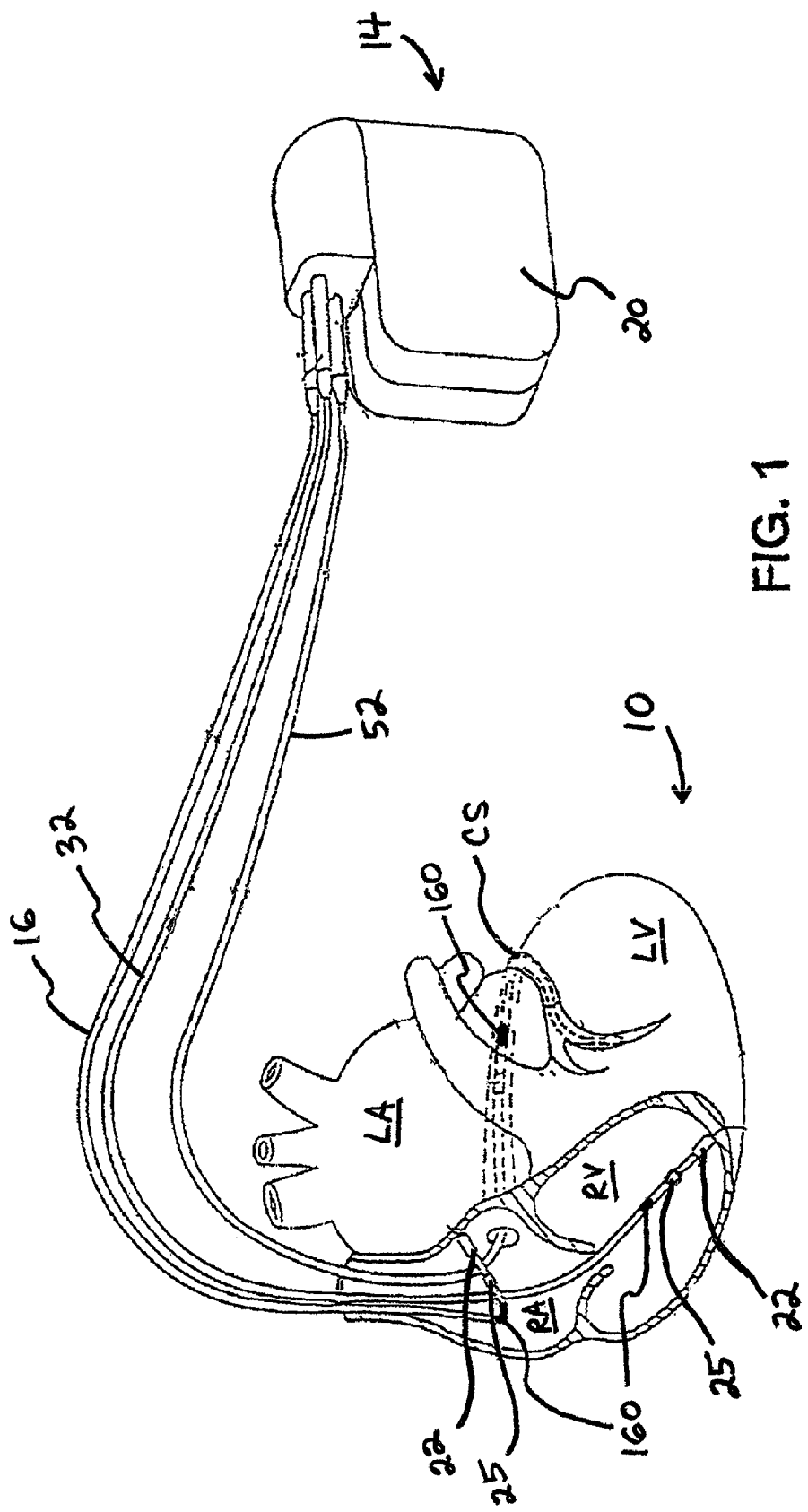
FIG. 1 is a schematic diagram depicting a multi-channel, atrial and bi-ventricular, monitoring/pacing IMD in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

The service life of an implantable medical device with digital signal processing (DSP) capabilities can be increased by selective implementation (e.g., enabling and/or disabling) of the DSP circuits. For example, DSP circuits associated with functions that a patient does not need can be disabled to reduce current drain. Certain embodiments of the invention may include, or may be adapted for use in, implantable medical devices (IMDs) with or without transvenous leads, including implantable hemodynamic monitors (IHMs), implantable cardioverter-defibrillators (ICDs), cardiac pacemakers, cardiac resynchronization therapy (CRT) pacing devices, implantable subcutaneous monitoring devices (e.g. Medtronic Reveal), implantable subcutaneous therapy devices (e.g. such as the defibrillation devices described in U.S. Pat. Nos. 6,647,292, 6,721,597, and 6,856,835, the relevant contents of each of which is hereby incorporated by reference), drug delivery devices, or combinations of such devices.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and/or other signals, such as the patient's intracardiac and/or subcutaneous electrogram (EGM) or electrocardiogram (ECG).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes, including electrodes integrated into or mounted on or around IMD 14 and non-transvenous and/or subcutaneous only electrodes.

It should be noted that the IMD 14 may also be an implantable cardioverter defibrillator (ICD), a cardiac resynchronization therapy (CRT) device, an implantable hemodynamic monitor (IHM), a subcutaneous monitoring or therapy device (e.g., defibrillation device with no intracardial or epicardial leads), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The electrodes and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
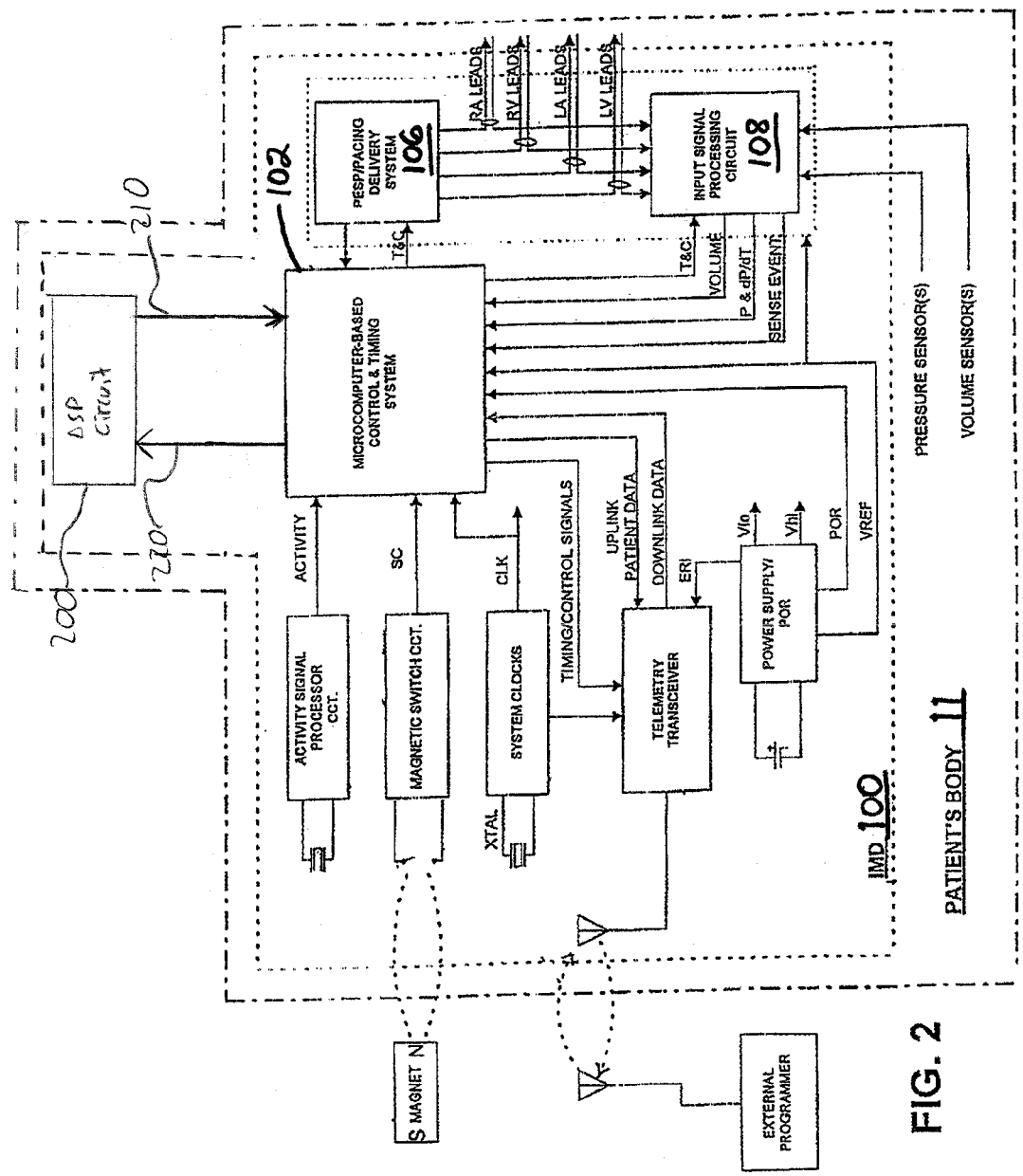
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary embodiment of a multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 (sometimes referred to herein as a microprocessor) which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation. Therapy delivery system 106 can also include a neurological stimulator. Other embodiments of the invention include a monitoring only implantable medical device.

The input signal processing circuit 108 includes at least one physiologic sensor signal processing channel for sensing and processing a sensor derived signal from a physiologic sensor located in relation to a heart chamber, under the skin or muscle (subcutaneous) or elsewhere in the body. Examples illustrated in FIG. 2 include pressure and volume sensors, but could include other physiologic or hemodynamic sensors such as a pulse oximeter and/or an accelerometer.

Figure 3:
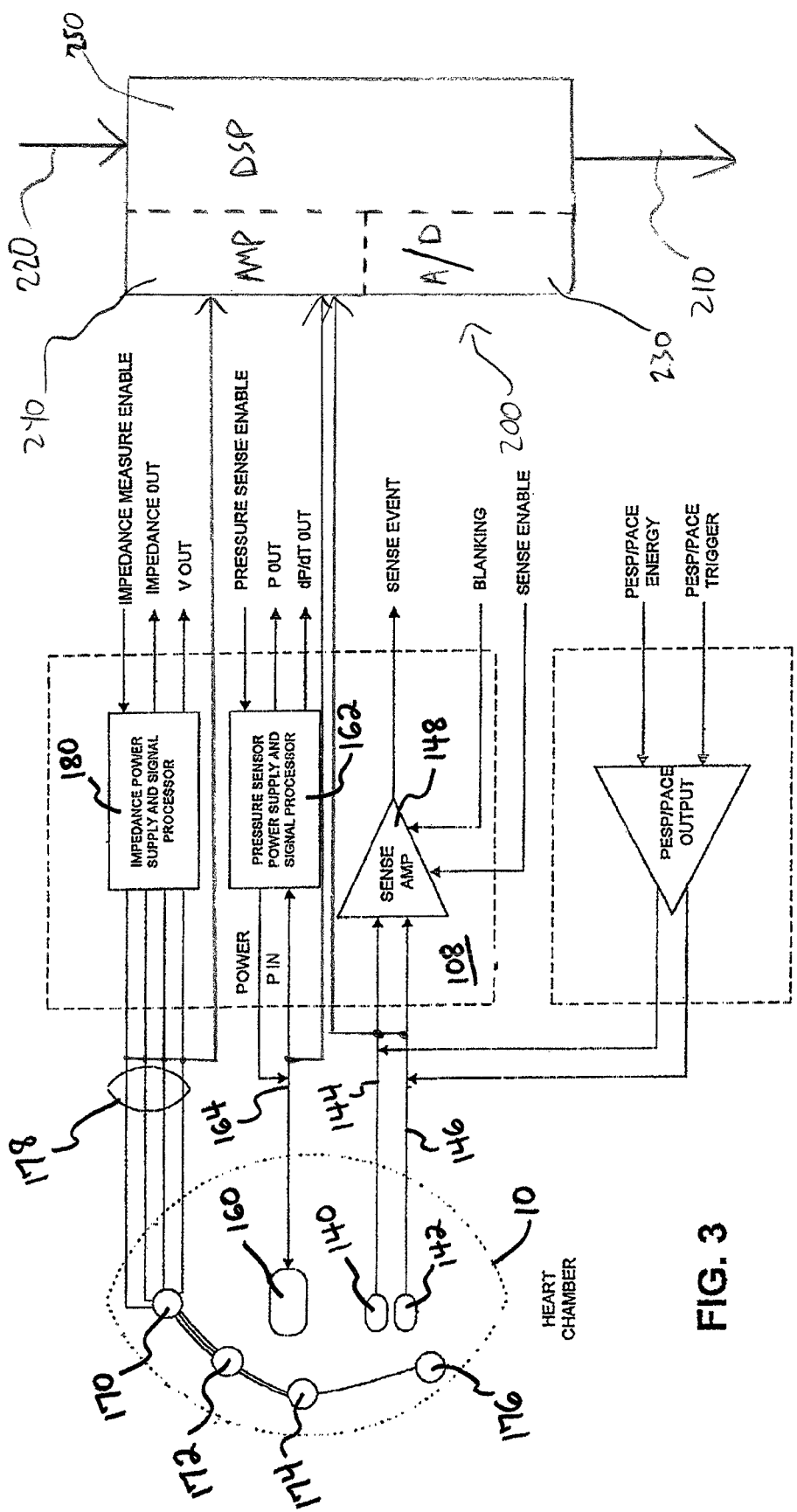
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber in accordance with an embodiment of the invention. A pair of pace/sense electrodes 140, 142, a pressure sensor 160, and a plurality, e.g., four, impedance measuring electrodes 170, 172, 174, 176 are located in operative relation to the heart 10.

In the embodiment of FIG. 3, the pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is enabled by the presence of a sense enable signal that is provided by control and timing system 102. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. In some embodiments, the control and timing system responds to non-refractory sense events by restarting an escape interval (EI) timer timing out the EI for the heart chamber, in a manner well known in the pacing art. In some embodiments, the control and timing system includes a timer that periodically polls or processes signals.

In the embodiment of FIG. 3, the pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, pulse oximetry (within the heart or placed subcutaneously to measure tissue perfusion) and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 may be coupled by a set of conductors 178 and be formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein, attached to the epicardium around the heart chamber, or placed subcutaneously. The impedance lead may be combined with the pace/sense and/or pressure sensor bearing lead.

The data stored by IMD 14 may include continuous monitoring of various parameters, for example recording intracardiac or subcutaneous EGM of ECG data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values (during that 6 minute period) are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

In some embodiments, the IMD 14 is provided with one or more selectively implementable DSP circuits 200. DSP circuits provide several advantages over analog circuits, including the capability of performing higher level functions and easier manufacturability and smaller size. The longevity of an IMD can be increased by selectively implementing the DSP circuits based on patient indication and/or automatically by device monitoring of changes in the patient's condition. For example, DSP circuits associated with functions that a patient does not need can be disabled to reduce current drain. In some embodiments, a "one size fits all" IMD can be provided. In such embodiments, an IMD is provided with several DSP circuits associated with several functions, and functions associated with DSP circuits are enabled or disabled to customize the IMD to the individual patient.

In some embodiments, the DSP circuit performs mathematical calculations on a stream of data (e.g., a digital representation of a waveform) and feeds a processed data stream to a microprocessor. Examples of data include intracardiac and/or subcutaneous EGMs or ECGs, pressure data, chemical sensor data, accelerometer data, and combinations thereof. In some embodiments the DSP circuits are repeated for each channel and in other embodiments are shared between channels (e.g., via multiplexing of data).

Embodiments of IMDs having selectively implementable DSP circuits will reduce current drain compared to IMDs having DSP circuits that are not selectively implementable. For example, in some embodiments each digital channel uses 700 nanoamps (nA), 100 nA of which is DSP. Accordingly, disabling such a DSP circuit when its function is not needed will save energy and prolong the battery life of the IMD. In some embodiments, a selectively disabled DSP circuit is turned completely "off," and does not draw current until enabled. In such embodiments, about 100 nA of current will be saved.

An embodiment of an IMD 14 with a DSP circuit 200 is depicted in FIG. 2. As shown in FIG. 2, IMD 14 may include a microprocessor 102 in communication with a DSP circuit 200. The microprocessor 102 may be programmed to receive information from the DSP circuit via the DSP circuit inlet line 210. In some embodiments, the microprocessor 102 also includes an output to DSP circuit line 220 to communicate with and control the DSP circuit 200. In some embodiments, the microprocessor provides control of the selectively implementable DSP circuit, such as by turning it on or off. Further, in some embodiments, the microprocessor can also perform low level mathematical calculations, i.e., it will perform an algorithm on a set of numbers, but not continuously on a stream of data.

Although in the embodiment of FIG. 2 only one output and input line is shown, any number of DSP circuits and associated communication lines may be provided. Further, multiple lines can be provided to communicate with each circuit. In addition, although only the microprocessor is shown connected to the DSP circuit in FIG. 2, any other component of the IMD may be connected to the DSP circuit. For example, the DSP circuit 200 could be in communication with the telemetry receiver, the input signal processing circuit 108, the pacing delivery system 106 and/or any combination of lead connections.

An embodiment of a single monitoring and pacing channel for acquiring pressure, impedance and cardiac EGM signals employed in monitoring cardiac function and/or delivering therapy and including a DSP circuit is shown in FIG. 3. As shown, the DSP circuit 200 can be in electrical communication with one or more of the electrodes 140, 142, 160, 170, 172, 174, and 176. In some embodiments, when enabled, the DSP circuit continually receives data from one or more of these sources and processes the data before transferring an output to the microprocessor 102 via line 210. In some embodiments, the DSP circuit senses information and converts it from analog to digital. Once in digital form the DSP circuit can run its algorithm computations and supply the output to the microprocessor where the output can be used, for example, to modify a therapy.

The DSP circuit may comprise any electronics suitable for receiving and digitally processing a signal. In some embodiments, the DSP circuit includes an analog to digital converter 230 and an amplifier 240. A separate analog to digital converter and amplifier can be provided for each DSP circuit, or a common analog to digital converter or amplifier may be shared by several DSP circuits. The amplified digital signal may then be processed in the digital signal processor 250 and the processed data transferred to the microprocessor via line 210.

Any function can be associated with a selectively implementable DSP circuit 200. In some embodiments, computationally complex algorithms that are not needed by a significant fraction of patients or those that are only needed for patients with deteriorating medical condition present ideal candidates for association with a selectively implementable DSP circuit 200. For example, the selectively implementable DSP circuit can provide and/or include a discriminator, filter, peak detector, wavelet template matching, noise detection and rejection, and combinations thereof.

In some embodiments the DSP circuit 200 includes a discriminator. In such embodiments, the DSP circuit can discriminate between an oversensed event and a true event. Examples of these types of DSP circuits include ventricular T-wave oversensing and rejection (repolarization artifact can be seen on the ventricular lead, and could show as double-sensing R-wave if not rejected), atrial far field R wave oversensing and rejection, and ischemia detection. For example, in the case of tachyarrhythmia detection, not all patients benefit from complex SVT discrimination algorithms, oversensing rejection algorithms, and other diagnostics. DSP circuits associated with such features can be selectively implemented to provide only the algorithms the patient needs. Such selective implementation is useful for reducing the current drain in the IMD.

As discussed above the DSP circuits can be associated with a variety of functions. For example, the DSP circuit can include a filter, such as a highpass, lowpass, and/or bandpass filter. In some embodiments the DSP circuit includes a peak detector for filter and threshold detection capabilities. In other embodiments the DSP circuit provides wavelet template matching. Such circuits are useful for comparing morphologies of waves against those during normal heart rhythm. Further, other embodiments of DSP circuits provide noise detection and rejection. Such circuits are particularly useful when the patient is in a noisy (predictable or periodic noise) environment (e.g., 60 Hz, patient works near a transmitter).

The DSP circuits may be selectively implemented by any suitable method, such as automatically or manual programming. In some embodiments, the IMD itself automatically selectively implements the DSP circuits. In such embodiments, the IMD can be programmed to selectively implement certain DSP circuits after sensing certain events. For example, DSP circuits associated with detailed electrogram analysis can be enabled only when a particular analysis decision is needed (e.g., at tachycardic heart rates, such as after the third fast beat). The microprocessor can disable the DSP circuit after the decision has been made. Further, in some embodiments, a DSP circuit can be selectively implemented by a detection of a change in disease state.

An IMD can also automatically selectively implement the DSP circuit upon detection of impedance changes. In some embodiments, if significant impedance changes are detected the IMD enables a DSP circuit adapted to detect or confirm, for example, lead failures or fractures. As another change in impendence example, the DSP circuit could run an enhanced algorithm measuring thoracic impedance to check for fluid overload. In some embodiments, upon detection of a change in lead or thoracic impedance, the microprocessor selectively enables a DSP circuit that contains an algorithm for the forced sense of impedance, where a signal is periodically injected and the response measured. The microprocessor can selectively disable the DSP circuit after the investigation is complete.

In some embodiments, the DSP circuit is automatically selectively implemented by the IMD based on waveform patterns and/or heart rate in different chambers. For example, an arrhythmia may be indicated when not sensing 1 to 1 (P to R wave ratio). In some embodiments, a DSP circuit providing a discriminator is automatically enabled by the IMD when sensing a 2 to 1 (P to R wave ratio) to determine if the patient has an arrhythmia or if the high P to R wave ratio is attributable to far field R wave oversensing. The microprocessor can disable the DSP circuit after the determination has been made. Similarly, discrimination algorithms may not be needed when the heart rate in the atrium is slower than the heart rate in the ventricle and the microprocessor can disable DSP. In some embodiments, a primary DSP function may enable or disable other secondary DSP functions based on the findings of the primary DSP function.

In some embodiments, the DSP circuit is automatically selectively implemented by the IMD based on a series of waveforms. For example, if a patient has a history incorrectly identifying noise as a cardiac event, the microprocessor could selectively enable a DSP circuit to check for noise every time a fast beat is sensed. After the DSP circuit confirms whether the fast beat was attributable to noise it could be disabled until another fast beat is sensed.

In other embodiments, the DSP circuits are selectively implemented via manual programming. For example, a clinician may selectively implement a DSP circuit, such as through a programmer, at the time of IMD implantation. In some embodiments, the IMD is provided with all DSP circuits enabled and the clinician disables certain DSP circuits associated with IMD functions not needed by the patient. In other embodiments, the IMD is provided with DSP circuits a clinician can enable to optimize the IMD for the patient. Further, the clinician can change the processing capability of the IMD by selectively implementing DSP circuits in response to disease state changes after the IMD has been implanted.

In some embodiments, DSP circuits may be periodically selectively implemented, either by a clinician, patient, or automatically by the IMD itself. This periodic selective implementation may be done by any suitable method, such as with a programmer or patient activator (such as a key fob with pushbutton) or other patient companion device (e.g., indicated by another patient medical device).

In some embodiments, the DSP circuit may be periodically selectively implemented in response to the patient's environment. For example, a patient working in an environment with higher than normal levels of electromagnetic radiation might enable a DSP noise reduction circuit during the hours the patient is at work. In other embodiments, the patient can initiate DSP analysis to detect a problem when not feeling well (e.g., patient feels flutter).

In other embodiments, the IMD could selectively enable a DSP circuit to periodically check for noise and/or arrhythmias (e.g., once every minute for A fib and once every 10 seconds for V tachycardia), then selectively disable the DSP circuit. In some embodiments the IMD can selectively enable a DSP circuit to complete a periodic forced sense, in which a forced signal is introduced and the response (e.g., impedance response) measured. In some embodiments, the IMD trains itself to run appropriate level of analysis.

In addition, IMDs having selectively implementable DSP circuits are useful when a clinician, home monitoring system or other patient medical device detects a problem. In such embodiments, a DSP circuit adapted to solve the problem (such as by detecting the source of the sensed problem) may be selectively enabled.

In some embodiments, an IMD is provided with a plurality of DSP circuits that can be independently selectively implemented according to any of the various methods described above. For example, the IMD may have a first DSP circuit that is selectively implemented by a clinician at the time of implantation, a second DSP circuit that is periodically selectively implemented by the patient, and a third DSP circuit that is selectively implemented by the IMD itself.

Figure 4:
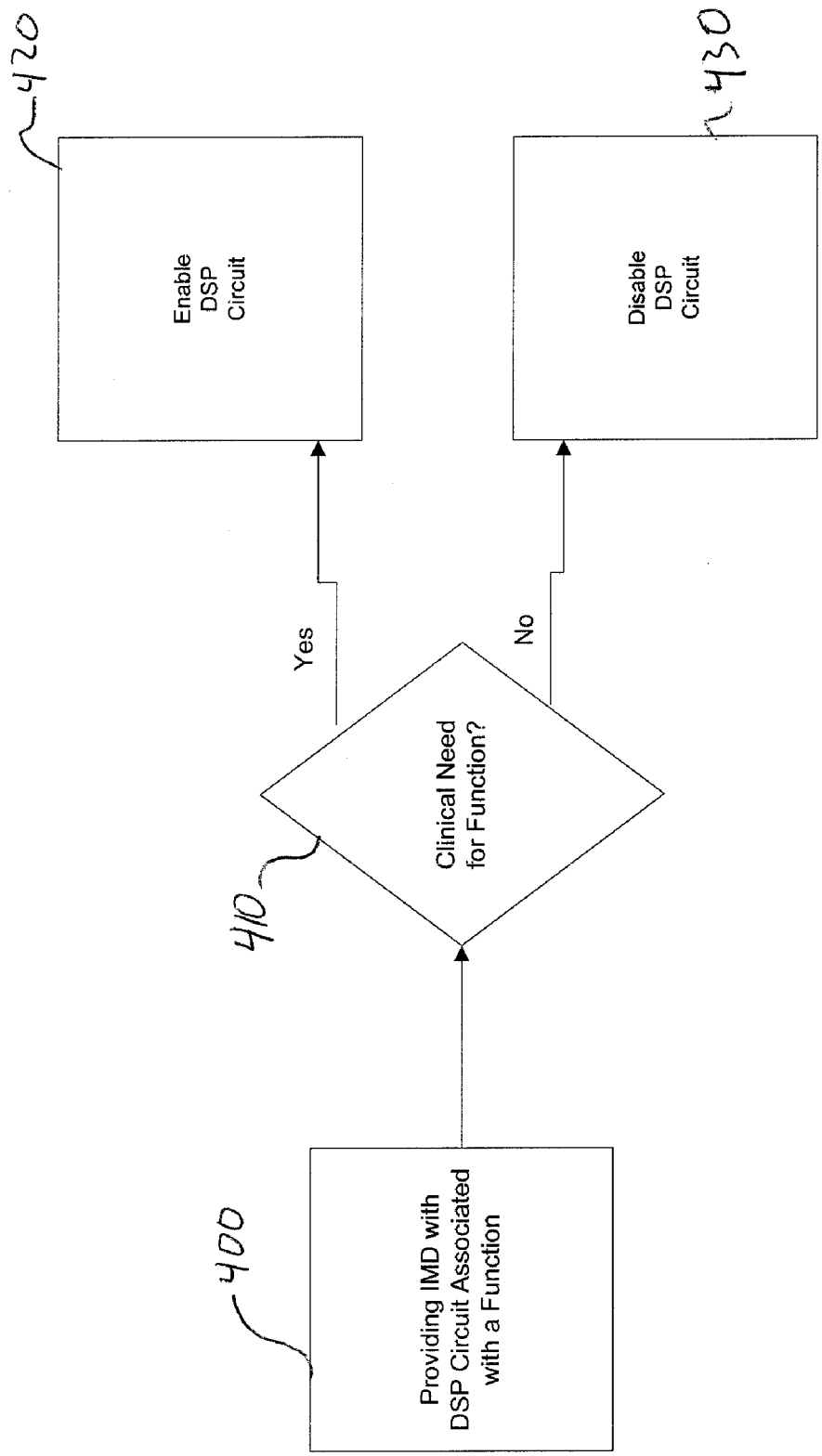
FIG. 4 is a flow chart depicting a method in accordance with an embodiment of the invention.

Some embodiments also include methods of making and using any of the various embodiments of the IMD with selectively implementable DSP circuits described above. For example, methods in accordance with embodiments of the invention include methods of reducing current drain of an IMD and methods of customizing an IMD to a patient. An example of a method of using such an IMD is shown in FIG. 4. As shown, some methods in accordance with embodiments of the invention include the step of providing an IMD with a DSP circuit associated with a function, as shown in block 400. Next, a determination is made whether there is a clinical need for the function, as depicted in block 410. As discussed above, this determination can be made either by a clinician, patient, or the IMD itself. If there is a clinical need for the function associated with the DSP circuit, the DSP circuit is enabled, as shown in block 420. If it is determined there is not a need for the function associated with the DSP circuit, the DSP circuit is disabled, as depicted in block 430. The DSP circuit may be enabled or disabled (i.e., selectively implemented) by any of the various methods described above, such as automatically by the IMD, manually programmed by a clinician, or periodically by a clinician, patient, or IMD.

Thus, embodiments of the SELECTIVELY IMPLEMENTABLE DIGITAL SIGNAL PROCESSING CIRCUIT FOR AN IMPLANTABLE MEDICAL DEVICE are disclosed. One skilled in the art will appreciate that the invention can be practiced with embodiments other than those disclosed. The disclosed embodiments are presented for purposes of illustration and not limitation, and the invention is limited only by the claims that follow.

What is claimed is:

1. An implantable medical device, configurable for a plurality of patients having a heart having characteristics and having a need for therapeutic treatment, having a plurality of functions, comprising:
   a hermetically sealed enclosure;
   a plurality of sensors configured to sense the characteristics of the heart;
   a plurality of digital signal processing circuits contained within the hermetically sealed enclosure, each individual one of the plurality of digital signal processing circuits being coupled to a respective one of the plurality of sensors, each individual one of the digital signal processing circuits providing, at least in part, an output related to an individual one of the plurality of functions, each individual one of the digital signal processing circuits being selectively turned off and drawing no current;

a processor coupled to each individual one of the plurality of digital signal processing circuits, the plurality of digital signal processing circuits being coupled between said plurality of sensors and said processor, wherein the processor is configured to process the output from each individual one of the plurality of digital signal processing circuits and to selectively turn off individual ones of the plurality of digital signal processing circuits based on the need for therapeutic treatment of an individual one of the plurality of patients for an individual one of the plurality of functions provided by the individual one of the plurality of digital signal processing circuits.

2. The implantable medical device of claim 1, wherein individual ones of the plurality of digital signal processing circuits comprise an analog to digital converter, an amplifier and a digital signal processor.

3. The implantable medical device of claim 1, wherein individual ones of the plurality of functions are selected from the group consisting of a discriminator, a filter, a peak detector, a wavelet template matcher, a noise detector and rejecter, and combinations thereof.

4. The implantable medical device of claim 1, wherein the implantable medical device is selected from the group consisting of hemodynamic monitors, cardioverter-defibrillators, cardiac pacemakers, cardiac resynchronization therapy pacing devices, drug delivery devices, subcutaneous monitoring devices, subcutaneous therapy devices, and combinations of such devices.

5. The implantable medical device of claim 1, further comprising a user input, the user input being associated with the plurality of digital signal processing circuits, wherein the need is determined, at least in part, based on a user indication via the user input.

6. The implantable medical device of claim 1, further comprising a processor, the processor being associated with the plurality of digital signal processing circuits, wherein the need is determined, at least in part, by the processor.

7. A method for configuring to meet a therapeutic need of a patient having a heart having characteristics an implantable medical device having a plurality of sensors sensing the characteristics of the heart, a plurality of digital signal processors each coupled to a respective one of the plurality of sensors, each individual one of the plurality of digital signal processors providing, at least in part, an output relating to an individual one of the plurality of functions, and a processor coupled to the plurality of digital signal processors, the plurality of digital signal processors being coupled between the plurality of sensors and the processor, comprising the steps of:

determining which individual ones of the plurality of functions do not meet the therapeutic need of the patient;

turning off individual ones of the plurality of digital signal processors that provide, at least in part, the individual ones of the plurality of functions that do not meet the therapeutic need of the patient so that the individual ones of the plurality of digital signal processors which are off draw no current; and processing with the processor the output from each individual one of the plurality of digital signal processors not turned off.

8. The method of claim 7, further comprising the step of delivering a therapeutic output that meets the therapeutic need of the patient based, at least in part, on the processing of the output from each individual one of the plurality of digital signal processors not turned off.

\* \* \* \* \*